United States Patent

Noe et al.

Patent Number: 5,344,942
Date of Patent: Sep. 6, 1994

[54] REAGENTS FOR RACMATE RESOLUTION

[75] Inventors: Christian Noe, Frankfurt am Main; Günter Gmeiner, Baden, both of Fed. Rep. of Germany

[73] Assignee: Chemie Linz Gesellschaft m.b.H., Austria

[21] Appl. No.: 41,185

[22] Filed: Apr. 1, 1993

[30] Foreign Application Priority Data

Apr. 13, 1992 [AT] Austria ................................ 769/92

[51] Int. Cl.$^5$ .................. C07D 307/93; C07D 311/94
[52] U.S. Cl. ...................................... 549/386; 549/459
[58] Field of Search ................... 549/459, 386

[56] References Cited

U.S. PATENT DOCUMENTS 4,497,960  2/1985  Noe ...................... 549/386

OTHER PUBLICATIONS

Chem. Abst. 109:92692x (1988).
Chem. Abst. 107:23537x (1987).
Chem. Abst. 105:208540v (1986).
Chem. Abst. 97:6085f (1982).

Primary Examiner—Bernard Dentz
Attorney, Agent, or Firm—Wenderoth, Lind & Ponack

[57] ABSTRACT (R) and (S) enantiomers of the formula

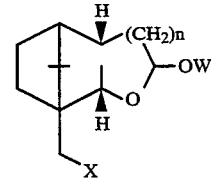

I in which
  n is 1 or 2,
  W is as defined in the specification which are characterized in that X is halogen, $SO_3H$, $SO_2Cl$ or $SO_2NR_1R_2$ where $R_1$ and $R_2$ are, independently of one another, hydrogen, substituted or unsubstituted, branched or unbranched alkyl, substituted or unsubstituted aryl or heteroaryl, or $R_1$ and $R_2$ form, together with the nitrogen, a substituted or unsubstituted heterocycle, a process for their preparation and their use for racemate resolution.

2 Claims, No Drawings

REAGENTS FOR RACMATE RESOLUTION

The present invention relates to reagents for racemate resolution which react with distinct preference for one of the enantiomers in a racemic mixture, to a process for their preparation and their use.

U.S. Pat. No. 4,497,960 discloses (R) and (S) enantiomers in which a 5- or 6-membered lactol ring is fused in cis configuration to a bornane ring, as well as their anhydro compounds, which can be employed as acetal protective groups and as reagents for racemate resolution and asymmetric induction. These compounds react with alcoholic and acid hydroxyl groups, with amino or mercapto groups of racemic compounds frequently with a selectivity which differs from the 1:1 ratio. However, the extent of this selectivity is usually so small that the effect is advantageous to only a limited extent for racemate resolutions.

The present invention relates to (R) and (S) enantiomers of the formula

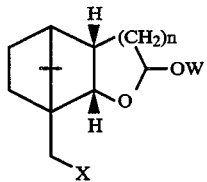

I in which
n is 1 or 2,
W is hydrogen, alkyl, cycloalkyl or the radical

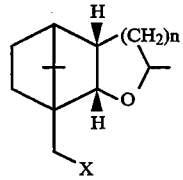

Ia and, in the case where W is hydrogen, their anhydro compounds of the formula

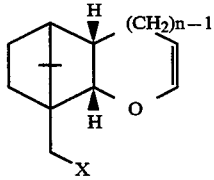

II in which n is as defined above, which are characterized in that X is halogen, $SO_3H$, $SO_2Cl$ or $SO_2NR_1R_2$ where $R_1$ and $R_2$ are, independently of one another, hydrogen, substituted or unsubstituted, branched or unbranched alkyl, substituted or unsubstituted aryl or heteroaryl, or $R_1$ and $R_2$ form, together with the nitrogen, a substituted or unsubstituted heterocycle.

In this connection, W is hydrogen, the radical of the formula Ia or an alkyl or cycloalkyl radical, preferably with 1-20 C atoms, particularly preferably with 1-10 C atoms, which can optionally be substituted, for example by hydroxyl, $COOR_3$ or amino. The alkyl radical and the cycloalkyl radical can moreover be branched or unbranched. Examples of alkyl and cycloalkyl radicals are methyl, ethyl, n-propyl, i-propyl, cyclopropyl, n-butyl, sec. butyl, tert. butyl, cyclobutyl, pentyl, cyclopentyl, hexyl, cyclohexyl, heptyl, cycloheptyl, decyl, cyclodecyl, dodecyl and octadecyl. $R_3$ can moreover be hydrogen or $(C_1-C_6)$alkyl.

X is halogen such as bromine, chlorine, fluorine and iodine, preferably bromine, furthermore $SO_3H$, $SO_2Cl$ or the group $SO_2NR_1R_2$. $R_1$ and $R_2$ can moreover be, independently of one another, hydrogen or an alkyl radical, preferably with 1-20 C atoms, particularly preferably with 1-10 C atoms, which can optionally be substituted, for example by hydroxyl, amino, $COOR_3$, $CONR_4R_5$ or aryl such as, for example, phenyl. The alkyl radical can moreover be branched or unbranched. $R_1$ and $R_2$ can also be an aryl radical with, preferably, 6-10 C atoms, such as, for example, a phenyl or naphthyl radical which can optionally be substituted by, for example, hydroxyl, $COOR_3$, amino or $(C_1-C_6)$alkyl. They can furthermore be a heteroaryl radical, preferably 5- or 6-membered, with O, N or S as heteroatom. $R_3$ has the above meaning in this connection. $R_4$ and $R_5$ can be, independently of one another, hydrogen, $(C_1-C_6)$alkyl, phenyl or benzyl. Examples of a heteroaryl radical are pyrrolyl, furanyl, thienyl, pyrazolyl, isoxazolyl, isothiazolyl, imidazolyl, pyridinyl, pyridazinyl, pyrimidinyl and pyrazinyl. However, $R_1$ and $R_2$ can also form, together with the nitrogen atom, a 3- to 7-membered heterocycle, preferably a 5- or 6-membered, which can optionally be substituted by $COOR_3$, where $R_3$ has the above meaning. Examples are aziridinyl, pyrrolidinyl, piperidinyl, proline or proline methyl or ethyl ester.

Preferred compounds of the formulae I and II are those in which W is hydrogen or the radical of the formula Ia, and X is the group $SO_2NR_1R_2$ where $R_1$ and $R_2$ are, independently of one another, hydrogen or a branched or unbranched $(C_1-C_{10})$alkyl which is unsubstituted or substituted by $COOR_3$, $CONR_4R_5$ or phenyl, or where $R_1$ and $R_2$ form, together with the nitrogen atom, a 5- or 6-membered heterocycle which is optionally substituted by $COOR_3$. In this connection, $R_3$ is hydrogen or $(C_1-C_6)$alkyl, and $R_4$ and $R_5$ can, independently of one another, be hydrogen, $(C_1-C_6)$alkyl or benzyl.

Individual compounds which are particularly preferred are:
1. (2alpha,3a-alpha,4beta,7alpha,7a-alpha)-7-Bromomethyl-8,8-dimethyloctahydro-4,7-methanobenzofuran-2-ol
2. (2alpha,3a-alpha,4beta,7alpha,7a-alpha)-2-Octahydro-2-hydroxy-8,8-dimethyl-4,7-methanobenzofuran-7-ylmethanesulfonic acid
3. (2alpha(2'R*,3'aS*,4'S*,7'R*,7'aS*),3a-alpha,4beta,7alpha,7a-alpha)-2,2'-Oxybis(octahydro-8,8-dimethyl-4,7-methanobenzofuran-7-ylmethanesulfonyl chloride)
4. (2alpha,3a-alpha,4beta,7alpha,7a-alpha)-N,N-Dimethyl-(octahydro-2-hydroxy-8,8-dimethyl-4,7-methanobenzofuran-7-yl)methanesulfonamide
5. (2alpha,3a-alpha,4beta,7alpha,7a-alpha)-N,N-Diethyl-(octahydro-2-hydroxy-8,8-dimethyl-4,7-methanobenzofuran- 7-yl)-methanesulfonamide
6. (2alpha,3a-alpha,4beta,7alpha,7a-alpha)-N,N-Bis(-phenylmethyl)-(octahydro-2-hydroxy-8,8-dimethyl-4,7-methanobenzofuran-7-yl)methanesulfonamide
7. (2alpha(2'R*,3'aS*,4'S*,7'R*,7'aS*),3a-alpha,4beta,7alpha,7a-alpha)-2,2'-Oxybis(N-(octahydro-8,8- dimethyl-4,7-methanobenzofuran-7-ylmethylsulfonyl)-N-(phenylmethyl)-glycine)
8. (2alpha(2'R*,3'aS*,4'S*,7'R*,7'aS*),3a-alpha,4beta, 7alpha,7a-alpha)-2,2'-Oxybis(1-(octahydro-8,8-dimethyl-4,7-methanobenzofuran-7-ylmethylsulfonyl)-L-proline methyl ester)
9. (2alpha(2'R*,3'aS*,4'S*,7'R*,7'aS*),3a-alpha,4beta, 7alpha,7a-alpha)-2,2'-Oxybis(1-(octahydro-8,8-dimethyl-4,7-methanobenzofuran-7-ylmethylsulfonyl)-L-proline)
10. (2alpha(2'R*,3'aS*,4'S*,7'R*,7'aS*),3a-alpha,4beta, 7alpha,7a-alpha)-2,2'-Oxybis(1-(octahydro-8,8-dimethyl-4,7-methanobenzofuran-7-ylmethylsulfonyl)-D-proline methyl ester)
11. (2alpha(2'R*,3'S*, 4'S*, 7'R*,7'aS*),3a-alpha,4beta, 7alpha,7a-alpha)-2,2'-Oxybis(1-(octahydro-8,8-dimethyl-4,7-methanobenzofuran-7-ylmethylsulfonyl)-D-proline)
12. (2alpha(2'R*,3'aS*,4'S*,7'R*,7'aS*),3a-alpha,4beta, 7alpha,7a-alpha)-2,2'-Oxybis(N-(octahydro-8,8-dimethyl-4,7-methanobenzofuran-7-ylmethylsulfonyl)-N-(2-methoxy-2-oxoethyl)-glycine methyl ester)
13. (2alpha(2'R*,3'aS*,4'S*,7'R*,7'aS*),3a-alpha, 4beta,7alpha,7a-alpha)-2,2'-Oxybis(N-(carboxymethyl)-N-(octahydro-8,8-dimethyl-4,7-methanobenzofuran-7-ylmethylsulfonyl)-glycine)
14. (2alpha(2'R*,3'aS*,4'S*,7'R*,7'aS*),3a-alpha,4beta, 7alpha,7a-alpha)-2,2'-Oxybis(octahydro-8,8-dimethyl-4,7-methanobenzofuran-7-ylmethylsulfonyl)-beta-alanine methyl ester)
15. (2alpha(2'R*,3'aS*,4'S*,7'R*,7'aS*),3a-alpha,4beta, 7alpha,7a-alpha)-2,2'-Oxybis(octahydro-8,8-dimethyl-4,7-methanobenzofuran-7-ylmethylsulfonyl)-beta-alanine
16. (2alpha(2 'R*,3'aS*,4'S*,7 'R*,7'aS*),3a-alpha,4-beta, 7alpha, 7a-alpha )-2,2'-Oxybis(octahydro-8,8-dimethyl-4,7-methanobenzofuran-7-ylmethylsulfonyl)-N-(phenylmethyl)-beta-alanine methyl ester)
17. (2alpha(2'R*,3'aS*,4'S*,7'R*,7'aS*),3a-alpha,4beta, 7alpha, 7a-alpha )-2,2'-Oxybis(octahydro-8,8'dimethyl-4,7-methanobenzofuran-7-ylmethylsulfonyl )-N-(phenylmethyl)-beta-alanine)
18. (2alpha(2'R*, 3'S*,4'S* ,7'R*,7'aS*),3a-alpha,4beta, 7alpha, 7a-alpha )-2,2'-Oxybis(2-N-(octahydro-8,8-dimethyl-4,7-methanobenzofuran-7-ylmethylsulfonyl-N-((phenylmethylamino)oxoethyl)-amino)acetamide)
19. (2alpha(2'R*,3'aS*,4'S*,7'R*,7'aS* ),3a-alpha,4beta, 7alpha, 7a-alpha) -2,2'-Oxybis(1-(1-(octahydro-8,8'dimethyl-4,7-methanobenzofuran-7-ylmethylsulfonyl)-L-prolyl)-L-proline methyl ester)

All the compounds of the formula I or II can be in the form either of the (R) or the (S) enantiomer.

The present invention also relates to a process for preparing compounds of the formula I, which is characterized in that a) a lactone of the formula

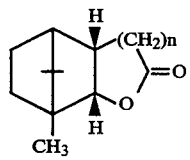

III in which n is as defined above, is reacted with a halogenating agent or with sulfuric acid and, where appropriate, subsequent conversion into the sulfonyl chloride to give a lactone of the formula

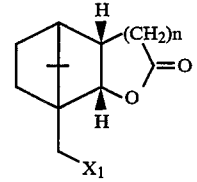

IV in which $X_1$ is halogen, $SO_3H$ or $SO_2Cl$, and n is as defined above, after which b) the lactone of the formula IV is reduced to a compound of the formula V

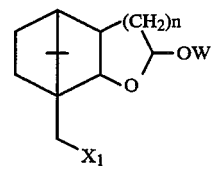

V in which W, n and $X_1$ are as defined above, and c) where appropriate the compound of the formula V is, in the case where $X_1$ is the group $SO_2Cl$, reacted with an amine of the formula $NHR_1R_2$    VI in which $R_1$ and $R_2$ are as defined above, to give a compound of the formula I, or d) the lactone of the formula IV is, in the case where $X_1$ is the group $SO_2Cl$, where appropriate first reacted with an amine of the formula VI to give a compound of the formula

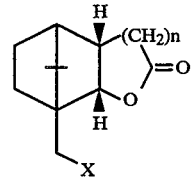

VII in which X and n are as defined above, and subsequently e) the compound of the formula VII is reduced to a compound of the formula I.

The lactone of the formula III used as starting material can be prepared, for example, as described in U.S. Pat. No. 4,497,960. The lactone can according to the invention be reacted in the first step with a halogenating agent, for example with bromine in the presence of red phosphorus. To do this, preferably the lactone and the phosphorus are introduced first and, with continuous stirring and cooling, preferably with cooling in ice, bromine is added dropwise. After the reaction which occurs during this has subsided, the reaction mixture is heated to about 50°-90° C., preferably 65°-75° C., a little bromine is again added, the temperature is raised slightly by about 10° C. and maintained at this temperature for 2 to 4 hours. Subsequently, the hydrogen bromide produced during this is removed from the reaction mixture by flushing with inert gas, for example with nitrogen. After the addition of small amounts of water, about 1-5 ml, the reaction mixture is exposed to water pump vacuum at about 120°–150° C., preferably 130°–140° C. The lactone of the formula IV is preferably isolated by extraction and subsequent recrystallization.

If the SO₃H or SO₂Cl group is to be introduced, the lactone of the formula III is sulfonated or sulfochlorinated. To do this, for example concentrated sulfuric acid is added to the lactone while cooling so that the temperature does not exceed 20° C. The reaction mixture is then left to stand at room temperature until the reaction is complete. After about 5–7 days, the resulting methanesulfonic acid lactone is filtered off with suction and washed. The methanesulfonic acid lactone can, if required, be converted into the sulfonyl chloride, for example using phosphorus pentachloride or other customary reagents.

A lactone of the formula IV obtained by one of the possibilities described above can then first be reduced to a lactol of the formula V.

Examples of suitable reducing agents are hydride compounds such as, for example, diisobutylaluminum hydride (DiBAl). To do this, the lactone is dissolved, for example in an anhydrous ether or in $CH_2Cl_2$, and then, under an inert gas atmosphere, for example $N_2$ atmosphere, preferably a DiBAl solution, for example in toluene, is added dropwise, during which the temperature is about −80° to −10° C. The lactol of the formula V obtained in this way is then isolated after about 0.5 to 2 hours preferably by extraction.

In order to obtain the self-condensed compounds of the formula I in which W is the radical of the formula Ia, for example a catalytic amount of a strong acid, for example 2N HCl, is added to the extractant during the extraction.

It is possible and preferred for lactols of the formula V in which $X_1$ is the group $SO_2Cl$ to be reacted with an amine of the formula VI. To do this, the appropriate methanesulfonyl chloride lactol is dissolved, for example in absolute ether or absolute $CH_2Cl_2$, 2–3 equivalents of the appropriate amine are added, and the resulting compound of the formula I is filtered off and purified, for example, by extraction and recrystallization. Examples of suitable amines are dimethylamine, diethylamine, dibenzylamine, phenylmethylglycine, proline methyl ester, proline, N-(2-methoxy-2-oxoethyl)glycine methyl ester, N-(2-carboxyethyl)glycine, alanine methyl ester, alanine, N-(phenylmethyl)alanine methyl ester, N-(phenylmethyl)alanine, leucine, N-((phenylmethylamino)oxoethyl)aminoacetamide or isoleucine.

The lactone of the formula IV can, however, in the case where $X_1$ is $SO_2Cl$ also be reacted first with an amine of the formula VI to give a compound of the formula VII in analogy to the procedure described above. The sulfonamide lactone prepared in this way is then cooled to about −70° to −50° C. under an inert gas atmosphere, and about 1–2 equivalents, preferably 1.5–1.7 equivalents, of a 2–3 molar, preferably 2.5 molar, DiBAl solution, for example in toluene, are slowly added. After 0.5 to 2 hours at −70° to −50° C., the compound of the formula I is isolated, preferably by extraction, and purified where appropriate by recrystallization.

The anhydro compounds of the formula II can be prepared, for example, from compounds of the formula I in which W is hydrogen, for example by adding dehydrating agents such as, for example, thionyl chloride.

The compounds of the formula I and II react with racemic compounds which contain a hydroxyl, carboxyl, amino or mercapto group with high selectivity, which makes it possible particularly easily to isolate one enantiomer pure.

The invention accordingly also relates to the use of compounds of the formula I or II for resolving racemic compounds which contain a hydroxyl, carboxyl, amino or mercapto group.

The compounds of the formula I and II are particularly suitable for resolving racemic compounds of the formula

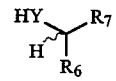

VIII in which Y is —O—, —S—, —COO— or —NH—. In this case, $R_4$ is preferably a "bulky" group, for example a branched or unbranched alkyl, preferably with 1–10 C atoms, which can optionally be substituted, for example by phenyl or $(C_1-C_6)$alkoxy. Examples are methyl, ethyl, n-propyl, i-propyl, sec.-butyl, t-butyl or hexyl. $R_7$ is preferably a "planar" or a "linear" group. These include aryls such as phenyl or heteroaryls such as, for example pyrrolyl or pyridinyl which can optionally be substituted by $(C_1-C_4)$alkyl, $(C_1-C_4)$alkoxy or hydroxyl, or —C≡N, —C≡C—, formyl, keto, carboxylic esters or amides which can optionally be substituted, for example by $(C_1-C_4)$alkyl. However, $R_6$ and $R_7$ can also both be chosen from the planar groups.

The invention also relates to a process for resolving racemic compounds which contain a hydroxyl, carboxyl, amino or mercapto group. The process is divided into 3 steps. Firstly, the compound of the formula I or II and the appropriate racemic compound are dissolved in suitable diluent, for example in anhydrous ether, dichloromethane, tetrahydrofuran, chloroform or in a petroleum ether/ether mixture (PE/E). After addition of triphenylphosphine hydrobromide (TPHB), the reaction mixture is stirred at room temperature for about 36–60 hours, preferably 48 hours. In the 2nd step, the reaction mixture is separated by extraction, and the final step comprises hydrolysis of the mixture of diastereomers by dissolving the mixture of diastereomers in a suitable solvent, heating to reflux, adding p-toluenesulfonic acid and maintaining at the reflux temperature for 3 to 8 hours. Subsequently alkali metal hydrogen carbonate or bicarbonate is added, and the pure enantiomers are isolated by extraction. The optical purity can be increased by a crystallization stage carried out before the hydrolysis.

EXAMPLE 1

Preparation of the Bromo Lactol (2S-(2alpha,3a-alpha,4beta,7beta,7a-alpha)-7-Bromomethyl-8,8-dimethyl-octahydro-4,7-methanobenzofuran-2-ol (n=1, W=H, X=Br)

16.5 g of bromine were added dropwise to a mixture of 20 g of (3aR-(3a-alpha,4beta,7beta,7a-alpha)-3a,4,5,6,7,7a)-hexahydro-7,8,8-trimethyl-4,7-methanobenzofuran-2(3H)-one and 1.3 g of red phosphorus while stirring and cooling in an ice bath, during which a very vigorous reaction started. After the reaction subsided, the mixture was heated to 70° C. and, at this temperature, another 16.5 g of bromine were added. After 3 hours at 80° C., the apparatus was flushed with nitrogen in order to drive out hydrogen bromide which had formed. Subsequently 2 ml of water were added and the reaction mixture was exposed to water pump vacuum at 135° C. until no further gas evolution was observed (about 4 hours). The mixture was then partitioned between dichloromethane and saturated sodium hydrogen carbonate solution, the aqueous phase was extracted with dichloromethane, and the combined organic phases were washed with water, dried and evaporated. The crude product (26.5 g, 94.2% of theory) was recrystallized from PE/E.

Yield: 19.1 g (67.9% of theory) of (3aS-(3a-alpha,4-beta, 7beta,7a-alpha))-7-bromomethyl-hexahydro-8,8-dimethyl-4,7-methanobenzofuran-2(3H)-one, colorless crystals, melting point 96°–100°C. (alpha))$_D^{20}$= −81.9° (c=0.68 in dichloromethane).

$^1$H-NMR (CDCl$_3$): delta=4.67 (d, J=8.8 Hz; 1H, H-7a), 3.80/3.68/3.44/3.32 (d, 2H, CH$_2$—Br), 1.1–2.6 (m, 8H, aliphatic H), 1.01/0.8 (2s, 6H, 2CH$_3$).

1.8 ml of a 1.2 molar solution of diisobutylaluminum hydride (DiBAl) in toluene were added dropwise to a solution of 500 mg of (3aS-(3a-alpha,4beta,7beta,7a-alpha)-7-bromomethyl-hexahydro-8,8-dimethyl-4,7-methanobenzofuran-2(3H)-one in 10 ml of anhydrous ether under a nitrogen atmosphere at −20° C. After 1 hour at −20 C., 1 ml of water was added, the reaction mixture was poured into 50 ml of ice-cold 10% acetic acid, and the aqueous phase was extracted with ether. The organic phase was washed with half-saturated sodium hydrogen carbonate solution until neutral. The aqueous phase was back-extracted with ether, and the combined organic phases were filtered with suction through 5 g of triethylamine-impregnated silica gel, dried and evaporated.

Yield: 491 mg (97.5% of theory) of (2S-(2alpha,3a-alpha,4beta,7beta,7a-alpha))-7-bromomethyl-8,8-dimethyloctahydro-4,7-methanobenzofuran-2-ol, colorless crystals, melting point 75°–78° C., (from petroleum ether/ether), (alpha)$_D^{20}$= −79.6° (c=0.22 in dichloromethane)

$^1$H-NMR (CDCl$_3$): delta=5.61 (t, J=5.0 Hz; 1H, 2-H), 4.40 (d, J=8.1 Hz; 1H, H-7a), 3.82/3.72/3.45/3.35 (d, 2H, CH$_2$Br), 2.7 (bs, 1H, OH), 1.1/2.5 (m, 8H, aliphatic H); 1.01/0.88 (2s, 6H, 2CH$_3$).

EXAMPLE 2

Preparation of the Sulfonyl Chloride Dilactol (2S-(2alpha(2'R*,3'aS*,4'S*,7'R*,7'aS*),3a-alpha,4-beta,-7alpha,7a-alpha))-2,2'-oxybis(octahydro-8,8-dimethyl4,7-methanobenzofuran-7-yl)methanesulfonyl chloride) (n=1, X=SO$_2$Cl, W=radical of the formula Ia)

0.85 ml of concentrated sulfuric acid was added dropwise to 1.05 g of acetic anhydride while cooling so that the temperature did not rise above 20° C. Subsequently 1 g of (3aR-(3a-alpha,4beta,7beta,7a-alpha)-3a,4,5,6,7-,7a)-hexahydro-7,8,8-trimethyl-4,7-methanobenzofuran-2(3H)-one was added, and the reaction mixture was left to stand at room temperature for 6 days. Filtration with suction and washing with anhydrous ether yielded 600 mg (42.5% of theory) of (3aS-(3a-alpha,-4beta,7beta,7a-alpha))-octahydro-8,8-dimethyl-2-oxo-4,7-methanobenzofuran-7-ylmethanesulfonic acid, colorless crystals, melting point 204° C. (from ethyl acetate, with decomposition (alpha)$_D^{20}$= −55.1° (c=1.34 in ethanol).

$^1$H-NMR (DMSO-d$_6$) after shaking with D$_2$O:delta=4.90 (d, J=8.4 Hz; 1H, H-7a), 3.03/2.87/2.63/2.47 (d, 2H, CH$_2$—SO$_3$), 1.1–1.9 (m, 8H, aliphatic H); 0.86 (s, 6H, 2CH$_3$).

100 mg of (3aS-(3a-alpha,4beta,7beta,7a-alpha)oc-tahydro-8,8-dimethyl-2-oxo-4,7-methanobenzofuran-7-ylmethanesulfonic acid were stirred with 77 mg of phosphorus pentachloride with exclusion of moisture while cooling in an ice bath. After 8 hours at room temperature, ice-water was added to the oily reaction mixture, whereupon a colorless precipitate formed. Filtration with suction and washing with ice-water yielded 80 mg (74.9% of theory) of (3aS-(3a-alpha,4-beta,7beta,7a-alpha)octahydro-8,8-dimethyl-2-oxo-4,7-methanobenzofuran-7-ylmethanesulfonyl chloride, colorless crystals, melting point 124°–127° C. (from dichloromethane/ether/petroleum ether), (alpha)$_D^{20}$= −62.6° (c=1.17 in ethyl acetate).

$^1$H-NMR (CDCl$_3$:delta=4.8–4.9 (m, 1H, H-7a), 4.36/4.21/3.83/3.68 (d, 2H, CH$_2$—SO$_3$), 1.1–2.9 (m, 8H, aliphatic H); 1.04/1.03 (2s, 6H, 2CH$_3$).

1.9 g of (3aS-(3a-alpha,4beta,7beta,7a-alpha)octahydro-8,8-dimethyl-2-oxo-4,7-methanobenzofuran-7-ylmethanesulfonyl chloride were dissolved in about 50 ml of abs. CH$_2$Cl$_2$ and cooled to −70° C. under an N$_2$ atmosphere. Then 4.8 ml of a 1.5 molar DiBAl solution in toluene were added dropwise so that the reaction temperature did not exceed −60° C. The mixture was stirred at −70° C. for one hour and then emptied into a mixture of 50 ml of CH$_2$Cl$_2$ and 50 ml of 2N HCl. The two phases were shaken until they were transparent, and the organic phase was washed once more with 2N HCl, dried over Na$_2$SO$_4$ and evaporated to dryness. The foam was digested in n-hexane, which resulted in it solidifying to a colorless powder.

Yield: 1.51 g (81% of theory) of (2S-(2alpha(2'R*,-3'aS*, 4'S*,7'R*,7'aS*),3a-alpha,4beta,7alpha,7a-alpha)-2,2'-oxybis(octahydro-8,8-dimethyl-4,7-methanobenzofuran-7-ylmethanesulfonyl chloride), colorless powder, melting point: 147°–152° C. (alpha)$_D^{20}$= −115° (c=3.26 in CH$_2$Cl$_2$), TLC: R$_f$=0.78 (PE/EE=3:1).

$^1$H-NMR (CDCl$_3$: delta=5.47 (d, J=2.5 Hz; 1H, H-2), 4.35 (d, J=12.5 Hz; 1H, CHSO$_2$), 4.30 (d, J=7.5 Hz; 1H, H-7a), 3.70 (d, J=12.5 Hz; 1H, CHSO$_2$), 2.38 (m; 1H, H-3a), 2.07 (m; 2H, H-3), 1.88 (m; 1H, H-6eq), 1.77 (m; 1H, H-4), 1.42 (m; 1H, H-5eq), 1.15 (m; 1H, H-6ax), 1.03/0.91 (2s; 6H, 2CH$_3$), 0.90 (m; 1H, H-5ax).

EXAMPLE 3

Preparation of Sulfonamide Lactols

General procedure for synthesizing the corresponding sulfonamide lactones

Absolute CH$_2$Cl$_2$ was added to a 5% strength suspension of (2S-(2alpha(2'R*,3'aS*,4'S*,7'R*,7'aS*),3a-alpha, 4beta, 7alpha, 7a-alpha ) -2,2'-oxybis(octahydro-8,8-dimethyl-4,7-methanobenzofuran-7-ylmethanesulfonyl chloride) in abs. ether until the product dissolved. Subsequently, 2–3 equivalents of the base were added, and the mixture was stirred overnight. The colorless precipitate was filtered off with suction, the reaction solution was concentrated and filtered through silica gel (solvent:ether), and the organic phase was washed with H$_2$O, dried over Na$_2$SO$_4$ and evaporated to dryness. The residue was recrystallized from n-hexane/toluene.

Example: (n=1, X=SO$_2$N(C$_2$H$_5$)$_2$): 2.66 ml (27.7 mmol) of diethylamine were added to a solution of 3.0 g (10.2 mmol) of (2S-(2alpha(2'R*,3'aS*,4'S*,7'R*,7'aS*)-,3a-alpha, 4beta, 7alpha, 7a-alpha))-2,2'-oxybis(octahydro-8,8-dimethyl-4,7-methanobenzofuran-7-ylmethanesulfonyl chloride), and the reaction mixture was treated further in accordance with the above procedure.

Yield: 2.4 g (71% of theory) of (3aS-(3a-alpha,4beta,-7alpha,7a-beta)-N,N-diethyl(octahydro-8,8-dimethyl-2-oxo-4,7-methanobenzofuran-7-yl)methanesulfonamide, colorless crystals, melting point 128°–130° C., (alpha)$_D^{20}$= −230° c=0.91 in $CH_2Cl_2$), TLC: $R_f$0.25 (E/-PE=9:1).

$^1$H-NMR ($CDCl_3$): delta=4.96 (s; 1H, H-7a), 3.30 (q; 2H, N—$CH_2$), 3.20 (q; 2H, N-$CH_2$), 3.25 (d, J=14 Hz; 1H, CH—$SO_2$), 2.76 (d, J=14 Hz, 1H, $CHSO_2$), 2.63–1.33 (m; 9H, aliphatic H), 1.22 (t; 6H, $CH_2\underline{CH_3}$), 0.97/0.93 (2s; 6H, $2CH_3$).

General procedure for the reduction of the sulfonamide lactones to the sulfonamide lactols An approximately 5% strength solution of the particular sulfonamide lactone prepared by the above procedure was cooled to −60° C. under an $N_2$ atmosphere, and 1.6 equivalents of a 2.5 molar diisobutylaluminum hydride solution in toluene were slowly added. The reaction mixture was then stirred at −60° C. for about 1 hour, partitioned between $CH_2Cl_2$/0.25N HCl and extracted with $CH_2Cl_2$. The organic phase was washed with $NaHCO_3$ and evaporated to dryness. The residue was recrystallized from toluene/n-hexane.

Example: (n=1, W=H, X=$SO_2N(C_2H_5)_2$): 2.24 g of (3aS-(3a-alpha,4beta,7alpha,7a-beta)-N,N-diethyl-(octahydro-8,8-dimethyl-2-oxo-4,7-methanobenzofuran-7-yl)methanesulfonamide were dissolved in 40 ml of abs. $CH_2Cl_2$ and treated further by the above procedure.

Yield: 1.90 g (85% of theory) of (2S-(2alpha,3a-alpha,4beta,7alpha,7a-alpha))-N,N-diethyl(octahydro-2-hydroxy-8,8-dimethyl-4,7-methanobenzofuran-7-yl)methanesulfonamide, colorless crystals, melting point: 129°–131° C., (alpha)$_D^{20}$= −211° (c=1.14 in $CH_2Cl_2$).

$^1$H-NMR ($CDCl_3$): delta=5.5 (dd; 1H, H-2), 4.59 (d; 1H, H-7a), 3.32 (d, J=14 Hz; 1H, $CHSO_2$), 3.31 (q; 4H, $NCH_2$), 2.68 (d, J=14 Hz; 1H, $CHSO_2$), 2.64–1.37 (m; 9H; aliphatic H, OH), 1.22 (t; 6H, $CH_2CH_3$), 0.97–0.84 (2s; 6H, $2CH_3$).

EXAMPLE 4

Preparation of the Sulfonamide Dilactols

General procedure for the synthesis of the sulfonamide dilactols 2 equivalents of the appropriate amine (free amine or hydrochloride) were added to an approximately 5% strength solution of (2S-(2alpha(2'R*,3'aS*,4'S*,7'R*,-7'aS*) ,3a-alpha,4beta,7alpha,7a-alpha)-2,2'-oxybis(octahydro-8,8-dimethyl-4,7-methanobenzofuran-7-ylmethanesulfonyl chloride) in abs. DMF, the reaction mixture was cooled to about 5° C. using an ice-water mixture, and 3 ( free amine ) or 5 (hydrochloride) equivalents of abs. triethylamine were injected. The reaction solution was stirred at the reaction temperature for 0.5 to 2 hours until the reaction was complete (TLC check) and then partitioned between ether and 0.5N HCl, and the org. phase was washed 2–3 times with 0.5N HCl, dried over $Na_2SO_4$ and evaporated to dryness. The residue (predominantly a colorless foam) was purified where appropriate by vacuum flash chromatography.

Example: (n=1, X=$SO_2$ (N-prolyl methyl ester)): 1 g of (2S-(2alpha(2'R*,3'aS*,4'S*,7'R*,7'aS*), 3a-alpha,4-beta,7alpha,7a-alpha))-2,2'-oxybis(octahydro-8,8-dimethyl-4,7-methanobenzofuran-7-ylmethanesulfonyl chloride), 1.8 g of L-proline methyl ester hydrochloride and 2.2 ml of triethylamine were stirred in accordance with the above general procedure for 2 hours.

Yield: 1 g (71% of theory) of (2S- (2alpha(2'R*,-3'aS*,4'S*,7'R*,7'aS*),3a-alpha,4beta,7alpha, 7a-alpha))-2,2'-oxybis(1-(octahydro-8,8-dimethyl-4,7-methanobenzofuran-7-ylmethylsulfonyl)-L-proline methyl ester), melting point: 81°–83° C. (alpha)$_D^{20}$=126° (C=0.79 in $CH_2Cl_2$).

$^1$H-NMR ($CDCl_3$): delta=5.43 (d; 1H, H-2), 4.51 (dd, $J_1$=9 Hz, $J_2$=3 Hz; 1H, H-alpha), 4.32 (d, J=7.5 Hz; 1H, H-7a), 3.74 (s; 3H, $OCH_3$), 3.57 (d, J=13 Hz; 1H, $CHSO_2$), 3.55 (m; 2H, H-delta), 3.06 (d, J=13 Hz; 1H, $CHSO_2$), 2.3 (m; 1H, H-beta), 2.25 (m; 1H, H-3a), 2.03 (m; 2H, H-3), 1.8–2.0 (m; 3H, H-beta, H-gamma), 1.72 (m; 1H, 6-6eq), 1.67 (m; 1H, H-4), 1.40 (m; 1H, H-5eq), 0.88 (m; 1H, H-5ax), 1.07 (m; 1H, H-6ax), 0.98/0.83 (2s; 6H, $2CH_3$).

General procedure for the hydrolysis of the dilactols with an ester functionality to the corresponding carboxylic acids:

3–5 equivalents of NaOH were dissolved in sufficient ethanol to result in an approximately 5% strength solution with the appropriate ester. This was followed by heating under reflux for 0.5 to 2 hours (TLC check), and the reaction solution was evaporated to dryness, taken up in $H_2O$, washed twice with ether, acidified to pH=1 with HCl and extracted with ether. The organic phase was dried over $Na_2SO_4$ and evaporated to dryness.

Example: (n=1, X=$SO_2$(N-proline), W=the radical of the formula Ia) in accordance with the general hydrolysis procedure, 1 g of (2S-(2alpha(2'R*,3'aS*,4'S*,7'R*,7'aS*),3a-alpha,4beta,7alpha,7a-alpha))-2,2'-oxybis(1-(octahydro-8,8-dimethyl-4,7-methanobenzofuran-7-ylmethylsulfonyl)-L-proline methyl ester) with 264 mg of NaOH.

Yield: 960 mg (quantitative) of (2S-(2alpha(2'R*,3'aS*,4'S*,7'R*,7'aS*),3a-alpha,4beta,7alpha,7a-alpha))-2,2'oxybis(1-(octahydro-8,8-dimethyl-4,7-methanobenzofuran-7-ylmethylsulfonyl)-L-proline), colorless foam, melting point: 121°–125° C., (alpha)$_D^{20}$=115° (c=1.04 in $CH_2Cl_2$).

$^1$H-NMR ($CDCl_3$): delta=9.1 (bs; 1H, COOH), 5.38 (s; 1H, H-2), 4.57 (dd, $J_1$=8 Hz, $J_2$=4.5 Hz; 1H, H-alpha), 4.4 (d, J=7 Hz; 1H, H-7a), 3.60 (d, J=13 Hz; 1H, $CHSO_2$), 3.5 (m; 2H, H-delta), 3.03 (d, J=13 Hz; 1H, $CHSO_2$), 2.31 (m; 1H, H-3a), 2.21 (m; 1H, H-beta), 1.8–2.04 (m; 2H, H-beta, H-gamma), 1.99 (m; 2H, H-3), 1.78 (m; 1H, H-6eq), 1.69 (m; 1H, H-4), 1.45 (m; 1H, H-5eq), 0.90 (m; 1H, H-5ax), 1.04 (m; 1H, H-6ax), 0.98/0.83 (2s; 6H, $2CH_3$).

EXAMPLE 5

Racemate Resolution by Extraction

The process is divided into three process steps:
1. acetalization
2. extractive separation and
3. hydrolysis Acetalization and extractive separation:

700 mg of (2S-(2alpha(2'R*,3'aS*,4'S*,7'R*,7,aS*)-,3a-alpha,4beta,7a-alpha))-2,2'-oxybis(1-((octahydro-8,8-dimethyl-4,7-methanobenzofuran-7-yl)methylsulfonyl)-L-proline) and 1.26 g of alpha-(1,1-dimethylethyl)benzenemethanol ($R_6$=t-Bu, $R_7$=Ph, Y=O) were dissolved in 30 ml of abs. dichloromethane and, after addition of 130 mg of triphenylphosphine hydrobromide (TPHB), the reaction mixture was stirred at room temperature for 48 hours. The reaction mixture was partitioned between PE/E=4:1 and a saturated KHCO3 solution, and the aqueous phase was extracted three times with PE/E=4:1 (ethanol added to improve phase separation), concentrated to one tenth the volume, acidified (pH <1) with 2N HCl, and extracted with CH2Cl2. The CH2Cl2 phase was dried over Na2SO4 and evaporated to dryness.

Yield: 1 g (100%) of 1-(2-(2,2-dimethyl-1-phenylpropoxy)octahydro-8,8-dimethyl-4,7-methanobenzofuran-7-ylmethylsulfonyl)-L-proline; ratio of (2S-(2alpha(R*),3a-alpha,4beta,7alpha,7a-alpha)) to (2S(2a(S*),3a-alpha,4beta,7alpha,7a-alpha))=7.2:1 (2S-(2alpha(R*),3a-alpha,4beta,7alpha,7a-alpha)); colorless crystals.

$^1$H-NMR (CDCl3): delta=4.88 (d, J=4.5 Hz; 1H, H-2), 4.55 (dd; 1H, H-alpha), 4.28 (s; 1H, H-C*), 3.58 (t; 2H, H-delta), 3.46 (d, J=13.5 Hz; 1H, CHSO2), 3.04 (d, J=13.5 Hz; 1H, CHSO2), 2.52–1.04 (m; 12 H, H-3, H-3a, H-4, H-5, H-6, H-beta, H-gamma), 0.87 (s; 9H, C(CH3)3), 0.87/0.8 (2s; 6H, 2CH3). (2S-(2alpha(S'),3a-alpha,4beta,7alpha,7a-alpha)).

$^1$H-NMR (CDCl3): delta=5.21 (d, J=5 Hz); 1H, H-2), 4.07 (d, J=6.5 Hz; 1H, H-7a), 4.05 (s; 1H, H-C*), 3.27 (d, J=14.5 Hz; 1H, CHSO2), 2.95 (d, J=14.5 Hz; 1H, CHSO2), 0.87/0.81 (2s; 6H, 2CH3).

The PE/E phase was likewise dried over Na2SO4 and evaporated to dryness.
Remaining alcohol: 865 mg (5.3 mmol; 93%).
Hydrolysis:

The mixture of diastereomers of 1-(2-(2,2-dimethyl-1-phenylpropoxy)-octahydro-8,8-dimethyl-4,7-methanobenzofuran-7-ylmethylsulfonyl)-L-proline was dissolved in 30 ml of CH3CN/H2O=4:1, heated to reflux and 150 mg of p-toluenesulfonic acid were added. After 5 hours under reflux, NaHCO3 was added to the reaction solution, which was then evaporated almost to drabness, and the residue was diluted with saturated NaHCO3 solution and extracted with ether. The organic phase was dried over Na2SO4 and evaporated to dryness. Eliminated alpha-(1,1-dimethylethyl)benzenemethanol: 300 mg (95%); S:R=6.9:1.

The aqueous phase was acidified with 2N HCl, extracted with CH2Cl2 and, after addition of a little toluene, dried over Na2SO4 and evaporated to dryness.

Recovered (2S-(2alpha(2'R*,3'aS*,4'S*,7'R*,7aS*)-,3a-alpha,4beta,7alpha,7a-alpha))-2,2,-oxybis(1-(octahydro-8,8-dimethyl-4,7-methanobenzofuran-7-ylmethylsulfonyl)-L-proline): 640 mg (91%).

EXAMPLE 6

Increasing the Optical Purity by Crystallizing the Enriched Mixture of Diastereomers The process consists of four steps:
1. acetalization
2. extraction
3. crystallization and
4. hydrolysis Acetalization and extraction:

6 g of (2S-(2alpha(2'R*,3'aS*,4'S*,7'R*,7,aS*),3a-alpha,4beta,7alpha,7a-alpha))-2,2,-oxybis(1-(octahydro-8,8-dimethyl-4,7-methanobenzofuran-7-ylmethylsulfonyl)-L-proline), 10.8 g of alpha-(1,1-dimethylethyl)-benzenemethanol (R6=t-Bu, R7=Ph, Y=O) and 550 mg of TPHB in CCl4 were stirred at room temperature for 4 days and, after addition of NaHCO3, the reaction mixture was evaporated to dryness and taken up in a saturated solution of KHCO3. The basic solution was extracted with PE/E with the addition of ethanol for phase separation, and the organic phase was evaporated to dryness, again taken up in ether, dried over Na2SO4 and evaporated to dryness. Remaining alcohol: 8.1 g (100%).

The aqueous phase was concentrated, acidified (pH <1) with 2N HCl and extracted with CH2Cl2. The organic phase was dried over Na2SO4 and evaporated to dryness.

Yield: 7.9 g (95%); ratio of (2S-(2alpha(R*),3a-alpha,4beta,7alpha,7a-alpha) to (2S-(2alpha(S*),3a-alpha,4beta,7alpha,7a-alpha))=10:1.
Crystallization:

The mixture of the diastereomeric acetals was crystallized from acetonitrile. The deposited crystals were filtered off and dried under water pump vacuum at 40° C.

Yield: 5.6 g (68%) of pure diastereomer (2S-(2alpha(R*),3a-alpha,4beta,7alpha,7a-alpha)-1-(2-(2,2-dimethyl-1-phenylpropoxy)-octahydro-8,8-dimethyl-4,7-methanobenzofuran-7-ylmethylsulfonyl)-L-proline; de>99%.
Hydrolysis:

The hydrolysis of the pure diastereomer (2S-(2alpha(R*),3a-alpha,4beta,7alpha,7a-alpha))-1-(2-(2,2-dimethyl-1-phenylpropoxy)-octahydro-8,8-dimethyl-4,7-methanobenzofuran-7-ylmethylsulfonyl)-L-proline was carried out in anology to the above procedure.

Yield: 3.9 g (65%) of (2S-(2alpha(2'R*,3'aS*,4'S*,7'R*,7'aS*),3a-alpha,4beta,7alpha,7a-alpha))-2,2'-oxybis(1-(octahydro-8,8-dimethyl-4,7-methanobenzofuran-7-ylmethylsulfonyl)-L-proline) and 1.7 g (65%) of S-alpha-(1,1-dimethylethyl)benzenemethanol; ee>99%.

Further racemate resolution examples were carried out in anology to Example 5 or 6 with different compounds of the formula I.

Furthermore, a comparative experiment with a compound from U.S. Pat. No. 4,497,960 which corresponds to a compound of the formula I of the present invention with X=hydrogen was carried out.

The results of the experiments for various racemic compounds of the formula

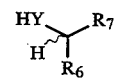

VIII in which Y is —O— are compiled in Table 1.

The numbering in this case corresponds to a numbering of the particularly preferred compounds on page 3-5.

The ratios indicate the (R) form:(S) form ratio in each case.

TABLE 1

|  |  | X |  |  |  |
|---|---|---|---|---|---|
|  |  | R6R7 |  |  |  |
|  |  | t-Bu/Ph | Me/Ph | Me/CN | m-PPh/CN |
| Comp. | H | 5.00:1 | 2.40:1 | 1.63:1 | 1.60:1 |
| 1 | Br |  | 3.20:1 | 2.60:1 |  |
| 4 | SO2NMe2 | 4.20:1 | 3.10:1 |  |  |

TABLE 1-continued

| | | X R₆R₇ | | | |
|---|---|---|---|---|---|
| | | t-Bu/Ph | Me/Ph | Me/CN | m-PPh/CN |
| 5 | SO$_2$NEt$_2$ | 6.27:1 | 3.60:1 | 4.20:1 | 2.70:1 |
| 6 | SO$_2$NBn$_2$ | 7.80:1 | 3.50:1 | 4.70:1 | 3.60:1 |
| 7 | SO$_2$N(Bn)CH$_2$COOH | 10.00:1 | 4.00:1 | 3.80:1 | 3.60:1 |
| 8 | SO$_2$(L-proline methyl ester) | 11.00:1 | 3.80:1 | 5.00:1 | 2.50:1 |
| 9 | SO$_2$(L-proline) | 7.75:1 | 3.50:1 | 2.70:1 | 2.80:1 |
| 10 | SO$_2$(D-proline methyl ester) | 9.00:1 | 3.00:1 | 3.00:1 | |
| 11 | SO$_2$(D-proline) | 14.00:1 | 3.50:1 | 3.40:1 | |
| 12 | SO$_2$N(CH$_2$COOMe)$_2$ | 11.00:1 | 4.30:1 | 4.10:1 | 2.70:1 |
| 13 | SO$_2$N(CH$_2$COOH)$_2$ | 7.70:1 | 4.40:1 | 2.90:1 | |
| 14 | SO$_2$NHCH$_2$CH$_2$COOMe | 4.90:1 | | | |
| 15 | SO$_2$NHCH$_2$CH$_2$COOH | 5.60:1 | 2.90:1 | 2.90:1 | |
| 16 | SO$_2$N(Bn)CH$_2$CH$_2$COOMe | 8.00:1 | 5.00:1 | 5.00:1 | |
| 17 | SO$_2$N(Bn)CH$_2$CH$_2$COOH | 9.00:1 | 3.10:1 | 3.10:1 | |
| 18 | SO$_2$N(CH$_2$CONHBn)$_2$ | 4.90:1 | 3.10:1 | 1.30:1 | 1.10:1 |
| 19 | SO$_2$(L-di-proline methyl ester) | 11.00:1 | 3.00:1 | 5.00:1 | 3.70:1 | t-Bu tertiary butyl
Ph phenyl
Me methyl
m-PPh meta-phenoxyphenyl
Bn benzyl

What we claim is:

1. An (R) or (S) enantiomer of the formula

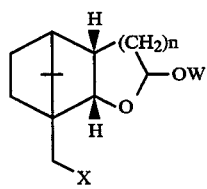

I in which
n is 1 or 2,
W is hydrogen, alkyl, cycloalkyl or the radical

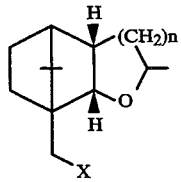

Ia and, in the case where W is hydrogen, their anhydro compounds of the formula

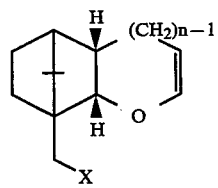

II in which n is as defined above, which are characterized in that X is halogen, SO$_3$H, SO$_2$Cl or SO$_2$NR$_1$R$_2$ where R$_1$ and R$_2$ are, independently of one another, hydrogen, substituted or unsubstituted, branched or unbranched alkyl, substituted or unsubstituted aryl or heteroaryl, or R$_1$ and R$_2$ form, together with the nitrogen, a substituted or unsubstituted heterocycle.

2. The (R) or (S) enantiomer and their anhydro compounds according to claim 1, characterized in that W is hydrogen or the radical of the formula Ia and X is the group SO$_2$NR$_1$R$_2$ in which R$_1$ and R$_2$ are, independently of one another, hydrogen, unbranched or branched (C$_1$-C$_{10}$)alkyl which can optionally be substituted by phenyl, COOR$_3$, or CONR$_4$R$_5$, where R$_3$ can be hydrogen or (C$_1$-C$_6$)alkyl and R$_4$ and R$_5$ can, independently of one another, be hydrogen, (C$_1$-C$_6$)alkyl or benzyl, or R$_1$ and R$_2$ form, together with the nitrogen, a 3-6 membered heterocycle which can optionally be substituted by COOR$_3$, where R$_3$ has the abovementioned meaning, and n is as defined in claim 1.

* * * * *